United States Patent [19]

DeForrest et al.

[11] Patent Number: 4,568,642

[45] Date of Patent: Feb. 4, 1986

[54] QUIET DENTAL DRILL

[75] Inventors: Allen L. DeForrest, Solvang; Raymond A. Amador, Santa Barbara; Dana R. Gawley, Clovis; Ralph J. Hoffman, Santa Barbara, all of Calif.

[73] Assignee: Advanced Dental Applications Corporation, Clovis, Calif.

[21] Appl. No.: 685,894

[22] Filed: Dec. 24, 1984

[51] Int. Cl.4 .......................... A61C 1/05; A61C 1/12
[52] U.S. Cl. ..................................... 433/132; 433/133
[58] Field of Search ................................ 433/132, 133

[56] References Cited

U.S. PATENT DOCUMENTS

| 1,878,747 | 9/1932 | Youngblood | 433/133 |
| 3,071,861 | 1/1963 | Saffir | 433/132 |
| 3,192,922 | 6/1965 | Winkler | 433/133 |
| 3,380,162 | 4/1968 | Heathe | 433/132 |
| 4,153,993 | 5/1979 | Kataoka et al. | 433/132 |

FOREIGN PATENT DOCUMENTS 925844  5/1963  United Kingdom ................ 433/132

Primary Examiner—Robert Peshock
Attorney, Agent, or Firm—Graybeal & Cullom

[57] ABSTRACT

A dental handpiece having a low noise level consisting of: an elongated main housing having a head portion at the forward end thereof; a drive shaft located within the main housing and supported by fore and aft bearings mounted within the main housing; a rotor/burr holder located within the head portion of the main housing and supported by bearings mounted within the head portion, the rotor/burr holder being adapted to receive a burr drill or the like; an air-driven axial flow turbine wheel located and supported within the rear portion of the main housing, the turbine wheel being operably connected to the drive shaft; and, a coupling system for operably coupling the forward portion of the drive shaft to the rotor/burr holder. In one embodiment of the invention, the coupling system consists of a set of cylindrical driving magnets mounted on the forward portion of the drive shaft and a corresponding set of cylindrical driven magnets mounted on the rotor/burr holder.

17 Claims, 7 Drawing Figures

U.S. Patent  Feb. 4, 1986  Sheet 1 of 2  4,568,642
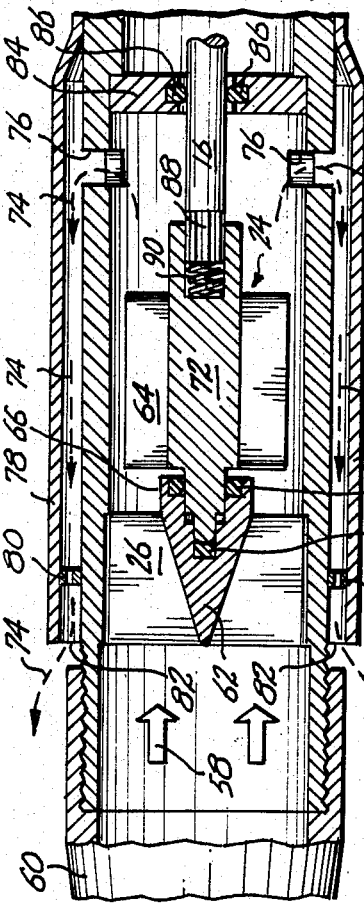

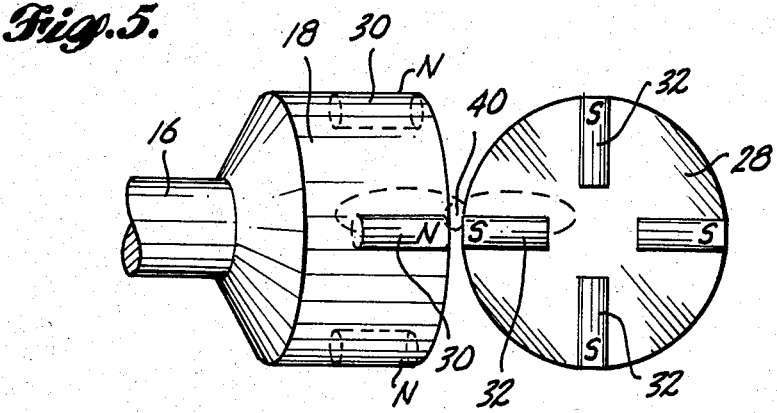
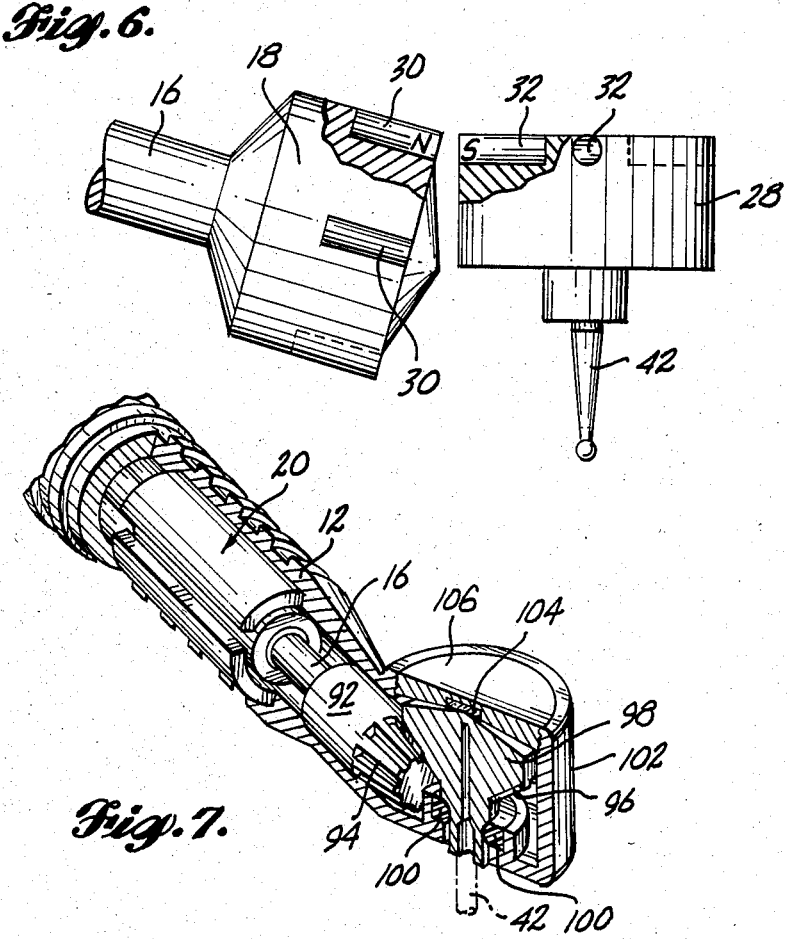

QUIET DENTAL DRILL

BACKGROUND OF THE INVENTION

1. Field of the Invention

This invention relates to the design and fabrication of air turbine dental handpieces ("dental drills"), and more particularly to a high speed air turbine dental handpiece having reduced noise levels.

2. Description of the Prior Art

Many dentists use a high speed air-driven impulse turbine dental handpiece in their practice to drill out cavities, to prepare crowns, and to drill holes for cap pinning. It is unfortunate that the prior art air turbine devices characteristically produce high noise levels that are systematically destroying the hearing of many dentists. The first high speed dental handpiece using an air-driven impulse turbine with jewel bearings was patented in 1963 by Dr. Jacob A. Saffir (U.S. Pat. No. 3,071,861), a dentist practicing in Los Angeles, California. Many of the prior art dental handpiece designs are modified versions of Dr. Saffir's design. There has been little or no improvement on the subject of drill noise reduction since 1963.

The conventional high speed dental handpieces manufactured today typically have the following common design features: (a) they use a 40 psig air supply; (b) they have an impulse turbine located in the drill head; (c) they use standard instrument ball bearings; (d) they have an uncontrolled air exhaust from the drill head; and, (e) they have a water mist system for burr cooling.

In the year 1983 there were approximately 35,000 licensed dentists in the State of California alone. Like other dentists worldwide, virtually all rely upon the pneumatic handpieces now on the commercial market. Nonetheless there is mounting evidence and a growing conviction among audiologists and dental personnel that the high noise levels produced by these conventional dental handpieces induce loss of hearing quite apart from damage due to natural causes.

In general, noise is undesirable because it may: (a) damage hearing, either temporarily or permanently; (b) mask other audible warning signals which ought to be heard, leading to confusion and causing accidents; (c) distract persons from concentration on important tasks and so cause mistakes and inefficient production; and, (d) hinder speech communication.

An important source of noise produced by conventional high speed dental handpieces is turbulence in the working fluid (air). Mechanical vibration of a surface is also a source of noise.

Pulsations and gas flow are generated by tangential flow turbo machinery because of their mode of operation. The noise frequency of pulsating flow is a multiple of the shaft speed and depends on the number of rotor blades. Pulsating flow produces noise as discrete frequencies corresponding to the fundamental frequency of the pulsations and its harmonics. This appears to be the primary noise source in the conventional dental handpiece although noise occurring over a band of frequencies, such as that produced by high speed jets, may also be a significant contributor.

Actual acoustic testing has shown that conventional high speed dental handpieces have not achieved their advertised noise levels of "less than 70 dBA". In fact, noise levels ranging from 76 dBA to 102 dBA at 4000 hz. have been measured.

Dental assistants also suffer the same plight as the dentist, i.e., irritability, fatigue, and gradual loss of hearing. Patients are not exposed for a long enough period of time to the high pitched sound to suffer hearing loss. However, patients experience an undeniable psychological effect due to the high pitched noise that can be described as negative. Patients are frequently afraid of the noise of the conventional high speed dental handpieces.

SUMMARY OF THE INVENTION

The present invention is a high speed air turbine dental drill which significantly reduces the level of operating noise. The impulse turbine located in the drill head of prior art dental handpieces has two negative features: (1) exhausting air from the drill head and (2) a pressure drop across the turbine blades which is essentially 40 psig. The present invention replaces the conventional impulse turbine with an axial flow turbine and relocates the turbine and the air exhaust therefrom to the remote end of the handpiece handle.

The axial flow turbine has a near zero pressure drop across its blades, which are shaped like air foils. Rotation of the turbine shaft is caused by the lift produced by the blade-foils. Air is not permitted to flow down the handle to escape from the drill head. Rather, the air is exhausted from the rear of the handle. The turbine position in the rear portion of the handle allows for a more efficient muffling of the air exhaust The quiet dental drill uses a combination of magnetic bearings and jewel bearings in place of the instrument ball bearings used in many conventional dental drills. The main drive shaft is located and supported by fore and aft magnetic bearings which provide reaction of radial loads. These bearings are spaced apart to avoid exciting the critical shaft speed in the region of operation. The magnetic bearings can be made of rare-earth permanent magnets, for example, samarium-cobalt magnets or neodymium-iron-boron magnets. Alternatively, recent developments in ball bearing technology make it feasible to use special high speed ball bearings to support the shaft, although the lower friction levels of magnetic bearings render them more desirable.

Transmission of torque from the main drive shaft to the rotor/burr holder is accomplished by a permanent magnetic coupling or "magnetic pinion". Here again rare-earth permanent magnets may be used. Other drive coupling means such as a bevel pinion gear - bevel ring gear type of drive coupling or a friction drive may also be used in place of the magnetic coupling.

BRIEF DESCRIPTION OF THE DRAWINGS

FIG. 1 is a perspective view of a first embodiment of the inventive quiet dental drill. Portions of FIG. 1 are in longitudinal section.

FIG. 2 is a cross-section along the line 2—2 shown in FIG. 1 through the aft magnetic bearing set.

FIG. 3 is an enlarged longitudinal sectional view of the rear portion of the quiet dental drill shown in FIG. 1 showing details of the turbine mount and drive shaft connection.

FIG. 4 is an enlarged longitudinal sectional view of the head portion of the quiet dental drill shown in FIG. 1.

FIG. 5 is an enlarged schematic plan view of a portion of the first embodiment of the invention showing the magnetic drive coupling.

FIG. 6 is an enlarged schematic side elevational view of the portion of the first embodiment of the invention shown in FIG. 5.

FIG. 7 is a perspective view of a second embodiment of the invention which uses a bevel pinion gear—bevel ring gear type of drive coupling. A portion of FIG. 7 is in longitudinal section.

DESCRIPTION OF THE PREFERRED EMBODIMENTS

The quiet dental drill is designed to operate in excess of 350,000 rpm free speed and to deliver 0.10 oz.-in. of torque at 250,000 rpm. The overall housing appearance and the weight of the quiet dental drill are similar to the conventional dental handpieces. Optional features, such as fiber optic lighting can readily be incorporated into the present invention. The quiet dental drill is designed to operate at measurably lower noise levels than all commercially available conventional high speed dental handpieces. Two embodiments of the inventive drill will now be described.

The First Embodiment (FIGS. 1-6)

The first embodiment is shown in FIGS. 1-6. Referring to the drawings, FIG. 1 shows the quiet dental drill 10. The drill 10 includes an elongate main housing 12 having a head portion 14. Main housing 12 encloses the drive shaft 16 (having an enlarged drive head 18 at the forward end thereof), the fore magnetic bearing set 20, the aft magnetic bearing set 22, the air-driven axial flow turbine 24, and the guide vanes 26. Drive shaft 16 is supported by fore magnetic bearing set 20 and aft magnetic bearing set 22 for rotational movement within main housing 12. The axis of drive shaft 16 intersects the axis of rotor/burr holder 28 which is supported for rotational movement within head portion 14. Mounted in the forward portion of drive head 18 are the cylindrical driving magnets 30 which are magnetically coupled with the corresponding cylindrical driven magnets 32 mounted in the rotor/burr holder 28 which rotates within head portion 14.

The components in head portion 14 and the magnetic coupling are shown in FIGS. 4, 5 and 6. The annular radial bearing 34 mounted within the head 14 and the thrust bearing or disc 36 mounted in head cap 38 are preferably made of a jewel material such as synthetic sapphire. Synthetic sapphire material has a low coefficient of friction and is now readily available at low cost from manufacturers which in the past have supplied meter movements to instrument manufacturers.

The driving magnets 30 and the driven magnets 32 are permanent magnets made from any suitable material and preferably are made from a rare-earth permanent magnetic material such as samarium-cobalt or neodymium-iron-boron. These rare-earth permanent magnet materials are described in more detail in Mechanical Engineering (August 1984) at pages 37-39 and in Machine Design (September 16, 1984) at pages 115-118.

As shown in FIGS. 1, 4, 5, and 6, the driving magnets 30 and the driven magnets 32 are cylindrical in shape in this first embodiment of the invention. FIG. 5 illustrates schematically the operation of the magnetic coupling or "magnetic pinion" which exists between driving magnets 30 and driven magnets 32. The magnetic coupling results from the magnetic force fields of driving magnets 30 and the magnetic force fields of driven magnets 32 (shown by the dashed lines in FIG. 5) which overlap and interact in the zone designated as 40.

The rotor/burr holder 28, which holds the burr drill 42 in a conventional way, is preferably made of a hard material, such as 440C stainless steel. The nose 44 of the drive head 18 and the surface 46 (FIG. 4) upon which it rests are likewise preferably hardened. The rotor/burr holder 28 is supported by the magnetic repulsion that exists between lower ring magnet 48 mounted within head 14 and upper ring magnet 50 mounted on rotor/burr holder 28.

The drive shaft 16 is supported by fore magnetic bearing set 20 and aft magnetic bearing set 22, which are identical in construction. These bearing sets 20 and 22 use the forces of magnetic repulsion to achieve a radial bearing effect. The aft magnetic bearing set 22 is shown in cross-sectional detail in FIG. 2. The cylindrical stationary magnets 52 are bonded inside the main housing 12. They are split to allow installation. The cylindrical rotating magnet 54 is bonded on the drive shaft 16. The air gap 56 is sized to allow magnetic repulsion to center the drive shaft 16 relative to the main housing 12. The stationary magnets 52 and the rotating magnet 54 may be rare-earth permanent magnets as described above. Alternatively, recent advances in ball bearing technology now make it feasible to employ special high speed ball bearings (not shown) to support the drive shaft 16, although the lower friction levels of the magnetic bearings render them more desirable.

The details of the turbine mount and the drive shaft connection are shown in FIG. 3. Compressed air 58 (for example, at 40 psig) is fed in through supply hose 60 connected to the threaded connection at the rear end of main housing 12. The guide vanes 26 and entrance fairing 62 are in one piece and have the function of straightening the incoming compressed air 58 before it meets the blades 64 of turbine 24 while at the same time the fairing 62 serves as a mount for the tail bearing housing 66 which houses the thrust bearing disc 68 and the radial bearing 70 which support the rear portion of the turbine shaft 72. The radial bearing 70 and the thrust bearing disc 68 are made preferably of a jewel material such as synthetic sapphire.

The guide vanes 26 are sized for a light press fit into the main housing 12 and are sufficiently thick to react the torque loads from the turbine 24. The maximum torque is about 0.20 oz.-in.

The turbine blades 64 are of classic air foil shape in order to provide adequate torque and speed but with only a minimal pressure drop across the blades. The lift due to proper camber and angle of attack of the blades 64 delivers the usable torque. The spent working air 74 exits through the exhaust ports 76 in the main housing 12. The outer shroud 78 directs the exhaust air 74 rearwardly, where it passes through an acoustic filter 80 and then finally exits to the atmosphere through annular opening 82. The acoustic filter or muffler 80, which is fitted inside the annular opening 82, consists of a flat stainless steel ring having many small axial perforations for the spent working air to pass through. The function of the acoustic filter 80 is to lower the noise level of the spent working air 74.

The annular housing member 84 (FIG. 3) is mounted inside the main housing 12. The flow restrictor 86 is mounted in the housing member 84 and forms a seal around the periphery of the drive shaft 16 so that the compressed air can not travel forward of the housing member 84, but rather must exit through the exhaust ports 76.

The rear end of drive shaft 16 (FIG. 3) has splines 88 which mesh with and are driven by corresponding internal gear teeth in the receiving bore of turbine shaft 72. Alternatively, instead of the splines 88, the rear end of drive shaft 16 and the receiving bore of turbine shaft 72 may be hexagonal in shape. Thrust spring 90 (FIG. 3) in the bore of turbine shaft 72 provides for a non-binding assembly or connection with drive shaft 16.

FIG. 5 shows an enlarged schematic plan view of the drive head 18 and the rotor/burr holder 28 in isolation. FIG. 6 shows an enlarged schematic side elevational view of drive head 18 and rotor/burr holder 28 in isolation with portions shown in section to reveal the construction. As described above, the driving magnets 30 are cylindrical or pole-shaped permanent magnets which are placed coaxially in four equally spaced apart locations around the periphery of drive head 18 at the front end of drive shaft 16.

The driven magnets 32 are similar cylindrical or pole-shaped permanent magnets placed radially in four equally spaced apart locations around the upper periphery of rotor/burr holder 28. The magnetic coupling results from the magnetic force fields of driving magnets 30 and the magnetic force fields of driven magnets 32 (shown by the dashed lines in FIG. 5) coming into contact and interacting in the zone designated as 40. The driving magnets 30 and the driven magnets 32 are permanent magnets made from any suitable material and preferably are made from a rare-earth permanent magnetic material such as samarium-cobalt or neodymium-iron-boron as described above.

The Second Embodiment (FIG. 7)

The second embodiment of the inventive quiet dental drill is shown in FIG. 7. In this embodiment, the forward portion of the drive head 92 of drive shaft 16 has bevel pinion gear teeth 94 which mesh with and drive the corresponding bevel ring gear teeth 96 on rotor/burr holder 98. Alternatively, instead of the bevel pinion gear - bevel ring gear arrangement, a frictional drive may be employed. The annular radial bearing 100 mounted in the head 102 and the thrust bearing or disc 104 mounted in head cap 106 are made preferably of a jewel material such as synthetic sapphire. The drive shaft 16 is supported by the fore magnetic bearing set 20 as described above. The rotor/burr holder 98 holds the burr drill 42 in a conventional way.

As will be apparent to those skilled in the art to which the invention is addressed, the present invention may be embodied in forms other than those specifically disclosed above without departing from the spirit or essential characteristics of the invention. The particular embodiments of the quiet dental drill, as described above, are therefore to be considered in all respects illustrative and not restrictive, with the scope of the present invention being set forth in the appended claims rather than being limited to the foregoing description.

What is claimed is:

1. A high speed dental drill having a low noise level, said drill comprising:
   (a) an elongated main housing having a head portion at the forward end thereof;
   (b) a drive shaft located within said main housing and supported by magnetic bearing means mounted within said main housing;
   (c) a rotor/burr holder located within said head portion of said main housing and supported by bearings mounted within said head portion, said rotor/burr holder being adapted to receive and hold a burr drill or the like;
   (d) an air-driven axial flow turbine mounted within the rear portion of said main housing, said turbine being operably connected to said drive shaft; and
   (e) magnetic coupling means for operably coupling the forward portion of said drive shaft to said rotor/burr holder.

2. The high speed dental drill of claim 1 wherein said main housing includes air exhaust means for exhausting spent working air toward the rear portion of said main housing.

3. The high speed dental drill of claim 2 wherein said air exhaust means further includes acoustic filter means for lowering the noise level of the spent working air.

4. The high speed dental drill of claim 1 wherein said bearing means supporting said drive shaft comprises a fore magnetic bearing set and an aft magnetic bearing set, wherein said magnetic bearing sets use the force of magnetic repulsion to achieve a radial bearing effect.

5. The high speed dental drill of claim 4 wherein said fore magnetic bearing set and said aft magnetic bearing set each comprise a stationary magnet mounted inside said main housing and a rotating magnet mounted on said drive shaft.

6. The high speed dental drill of claim 1, wherein said rotor/burr holder is supported by the force of magnetic repulsion exerted between a lower ring magnet mounted within said head portion of said main housing and an upper ring magnet mounted on said rotor/burr holder.

7. The high speed dental drill of claim 1 wherein said turbine has turbine blades shaped like air foils.

8. The high speed dental drill of claim 1 wherein said turbine is supported by a jewel radial bearing and a jewel thrust bearing.

9. The high speed dental drill of claim 1 wherein said magnetic coupling means comprises a plurality of cylindrical magnets mounted on the forward portion of said drive shaft and a plurality of cylindrical magnets mounted on said rotor/burr holder.

10. A high speed dental drill having a low noise level, said drill comprising:
    (a) an elongated main housing having a head portion at the forward end thereof;
    (b) a drive-shaft located within said main housing and supported by magnetic bearing means mounted within said main housing;
    (c) a rotor/burr holder located within said head portion of said main housing and supported by bearings mounted within said head portion, said rotor/burr holder being adapted to receive and hold a burr drill or the like;
    (d) an air-driven axial flow turbine mounted within the rear portion of said main housing, said turbine being operably connected to said drive shaft; and
    (e) mechanical coupling means for operably coupling the forward portion of said drive shaft to said rotor/burr holder, said mechanical coupling means comprising a plurality of bevel pinion gear teeth on the forward portion of said drive shaft and a plurality of bevel ring gear teeth on said rotor/burr holder which mesh with said bevel pinion gear teeth.

11. The high speed dental drill of claim 10 wherein said main housing includes air exhaust means for exhausting spent working air toward the rear portion of said main housing.

12. The high speed dental drill of claim 11 wherein said air exhaust means further includes acoustic filter means for lowering the noise level of the spent working air.

13. The high speed dental drill of claim 10 wherein said bearing means supporting said drive shaft comprises a fore magnetic bearing set and an aft magnetic bearing set, wherein said magnetic bearing sets use the force of magnetic repulsion to achieve a radial bearing effect.

14. The high speed dental drill of claim 13 wherein said fore magnetic bearing set and said aft magnetic bearing set each comprise a stationary magnet mounted inside said main housing and a rotating magnet mounted on said drive shaft.

15. The high speed dental drill of claim 10 wherein said rotor/burr holder is supported by the force of magnetic repulsion exerted between a lower ring magnet mounted within said head portion of said main housing and an upper ring magnet mounted on said rotor/burr holder.

16. The high speed dental drill of claim 10 wherein said turbine has turbine blades of air foil shape.

17. The high speed dental drill of claim 10 wherein said turbine is supported by a jewel radial bearing and a jewel thrust bearing.

* * * * *